United States Patent
Stromgren

(10) Patent No.: US 6,629,945 B1
(45) Date of Patent: Oct. 7, 2003

(54) STABILIZED ANKLE SUPPORT

(76) Inventor: Lawrence T. Stromgren, 109 LaChite #1, Horseshoe Bay West, TX (US) 78657

( * ) Notice: Subject to any disclaimer, the term of this patent is extended or adjusted under 35 U.S.C. 154(b) by 0 days.

(21) Appl. No.: 09/714,623

(22) Filed: Nov. 16, 2000

(51) Int. Cl.[7] .................................................. A61F 13/00
(52) U.S. Cl. .............................. 602/65; 602/60; 602/62; 602/5
(58) Field of Search .................. 602/5, 16, 20, 602/21, 23–29, 65–66, 75, 1, 60, 62; 128/876–878, 882, 846, 869, 889, 892–893, 894; 482/79, 105; 24/442, 306

(56) References Cited

U.S. PATENT DOCUMENTS

| | | | |
|---|---|---|---|
| 3,584,622 A | * | 6/1971 | Domenico |
| 4,179,826 A | | 12/1979 | Davidson |
| 4,237,874 A | | 12/1980 | Nelson |
| 4,280,489 A | | 7/1981 | Johnson, Jr. |
| 4,287,920 A | | 9/1981 | Johnson, Jr. |
| 4,367,733 A | | 1/1983 | Stromgren |
| 4,628,945 A | | 12/1986 | Johnson, Jr. |
| 4,727,863 A | | 3/1988 | Nelson |
| 4,962,768 A | | 10/1990 | Stromgren et al. |
| 4,974,343 A | | 12/1990 | Davidson |
| 5,007,416 A | | 4/1991 | Burns et al. |
| 5,125,400 A | | 6/1992 | Johnson, Jr. |
| 5,172,494 A | | 12/1992 | Davidson |
| 5,492,133 A | | 2/1996 | McVicker |

FOREIGN PATENT DOCUMENTS

CA     1160925     1/1984

* cited by examiner

*Primary Examiner*—Nicholas D. Lucchesi
*Assistant Examiner*—Lalita M. Hamilton
(74) *Attorney, Agent, or Firm*—Chase Law Firm, L.C.

(57) ABSTRACT

An ankle support is provided with a semi-rigid stabilizer having upstanding walls that present a generally U-shaped support structure conforming to the shape of a wearer's heel, and having an anterior mouth from which the wearer's foot projects. Medial and lateral walls of the stabilizer have peak portions at the mouth which extend into supporting relationship to the wearer beneath the medial and lateral malleolus to provide an effective heel lock. The upper edges of the supporting walls extend abruptly downwardly from the peak portions to a lower rear wall to provide relief at the rear of the stabilizer.

15 Claims, 2 Drawing Sheets

STABILIZED ANKLE SUPPORT

BACKGROUND OF THE INVENTION

This invention relates to improvements in ankle supports and, in particular, to a support that is provided with a stabilizer for receiving the heel and stabilizing the wearer's foot beneath the medial and lateral malleolus to lock the heel to the fibula and thereby control abnormal movement of the ankle.

Ankle supports of many different types are widely used and are commonly accepted in the sports medicine field as a means of protecting the ankle joint from injury due to a medial or lateral twisting or rollover during an athletic activity, whether of the contact or non-contact type. The supports are also used to assist in rehabilitation after an injury, and may be worn as well by active individuals not involved in competitive athletics.

The ultimate function of an ankle support is to control any abnormal movement of the ankle complex, and most importantly to lock the heel to the fibula. This is referred to as a "heel lock" by the training profession, and is what a competent trainer attempts to accomplish in the final steps of taping an athlete's ankle.

Taping of the ankle, however, is expensive and time-consuming because the adhesive tapes are not reusable and properly taping or supervising the taping is very time consuming. Reusable ankle wraps and supports are a solution to these problems and are widely used, such as supports of the type disclosed in U.S. Pat. Nos. 4,367,733 and 4,962,768. The ankle supports disclosed in these patents do an effective job of locking the heel bone to the fibula, but both have been found to be complicated for the average person to put on correctly. Furthermore, there are other ankle support products that provide effective medial and lateral support but fail to provide an effective heel lock. Accordingly, there exists a need for a reusable ankle support of simple configuration which provides both the medial/lateral protection and a heel lock to fully control abnormal movement of the ankle.

SUMMARY OF THE INVENTION

It is, therefore, the primary object of the present invention to provide an ankle support which is uncomplicated in design and application to a wearer's foot, and which provides both medial/lateral support and an effective heel lock.

As a corollary to the foregoing object, it is an important aim of this invention to provide a stabilized ankle support that includes a semi-rigid stabilizer for receiving a wearer's heel and providing support beneath the medial and lateral malleolus, in combination with a flexible ankle support extending upwardly from the stabilizer for providing medial and lateral support while the stabilizer locks the heel to the fibula.

Another important object of the invention is to provide a stabilized ankle support as aforesaid in which the stabilizer has medial and lateral support walls with peak portions that provide stability beneath the malleolus, and is configured to provide relief at the rear of the stabilizer so that it will not cause discomfort or blister the heel.

Another important object is to provide such a stabilizer that receives the heel only so that it does not affect the arch or anterior portions of the foot, thereby providing the desired stabilization and heel lock while allowing the wearer normal movement so as to not impede an athlete's speed or motion.

Still another important object is to provide an ankle support which locks the heel to the fibula, is simple to use and comfortable through the employment of a semi-rigid stabilizer that receives the heel and requires no adjustment, manipulation or taping.

Further objects will become apparent as the detailed description proceeds.

DETAILED DESCRIPTION

Figure 1:
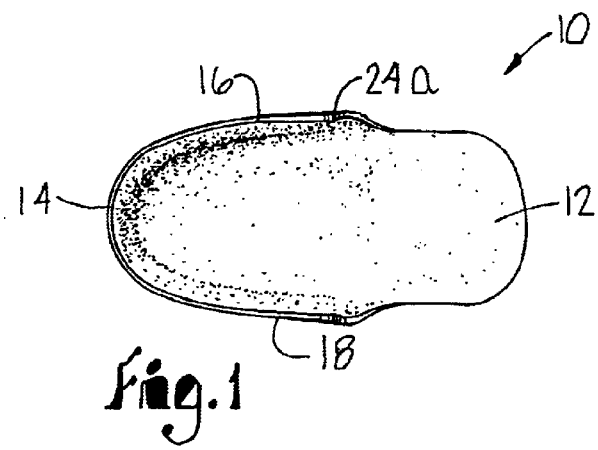
FIG. 1 is a top plan view of the semi-rigid stabilizer of the present invention, showing the same removed from the body of the ankle support.

Referring initially to FIGS. 1–4, the ankle stabilizer of the present invention is of unitary construction and is preferably composed of a molded plastic, semi-rigid material having sufficient flexibility to provide comfort in use. The stabilizer 10 has a flat base plate portion 12, a low, curved rear wall 14 and upstanding medial and lateral support walls 16 and 18. It may be appreciated that the rear, medial and lateral walls present a generally U-shaped support structure conforming to the shape of a wearer's heel and having an anterior mouth 20 from which the foot of the wearer projects when the ankle support is applied. The bottom edge of rear wall 14 is curved where it merges with base plate 12, and likewise the lower margins of side walls 16 and 18 are curved where they merge with base plate 12. Accordingly, a smooth transition from the horizontal base plate to the upstanding wall structure is provided.

Figure 3:
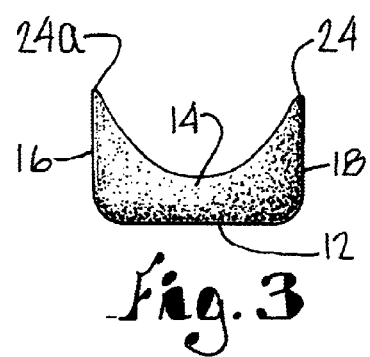
FIG. 3 is a rear elevational view of the stabilizer of FIG. 1.
Figure 2:
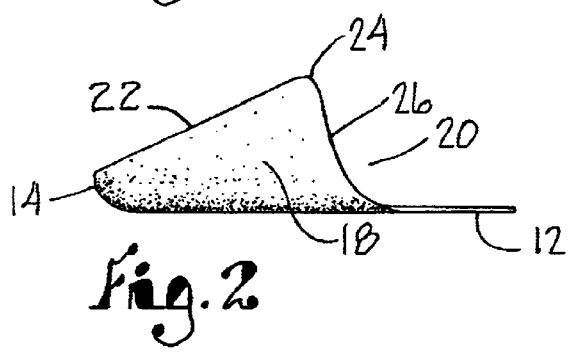
FIG. 2 is a side elevational view of the stabilizer shown in FIG. 1.
Figure 4:
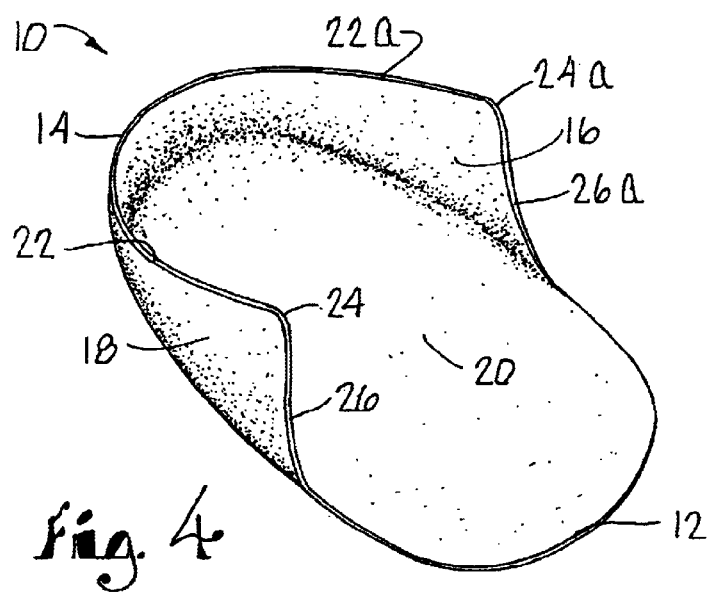
FIG. 4 is an enlarged, perspective view of the stabilizer of FIG. 1 as seen looking downwardly from the side into the anterior mouth thereof.

The side walls 16 and 18 and the rear wall 14 are specially configured as may be appreciated from a comparison of FIGS. 1–4. The lateral wall 18 has a straight upper edge 22 which extends upwardly from the rear wall at approximately a 25-degree to 30-degree angle with respect to the base plate 12. The edge 22 terminates at an apex or peak 24 just beneath the lateral malleolus 26 as will be discussed below with respect to FIG. 5. From peak 24 forward, wall 18 presents a nearly vertical terminal edge 26 that has a smooth, curved transition into base plate 12. The medial wall 16 has the same identical shape as lateral wall 18, as best seen in FIG. 4 where identical features are denoted by the same reference numerals with the addition of the "a" notation.

It is important to note that the height of the rear wall 14 at the rear of the stabilizer 10 is approximately one-third of the height of the peaks 24 and 24a above the base plate 12 (see FIG. 3). Accordingly, the upper edges 22 and 22a of the side walls extend abruptly downwardly from the peaks 24 and 24a to the lower rear wall 14, thereby providing relief at the rear of the stabilizer so that the rear wall 14 will not cause discomfort or blister the heel of the wearer. However, at the peaks 24 and 24a, the walls 16 and 18 are sufficiently high on the wearer's ankle to support the foot beneath the medial and lateral malleolus and provide an effective heel lock.

Figure 5:
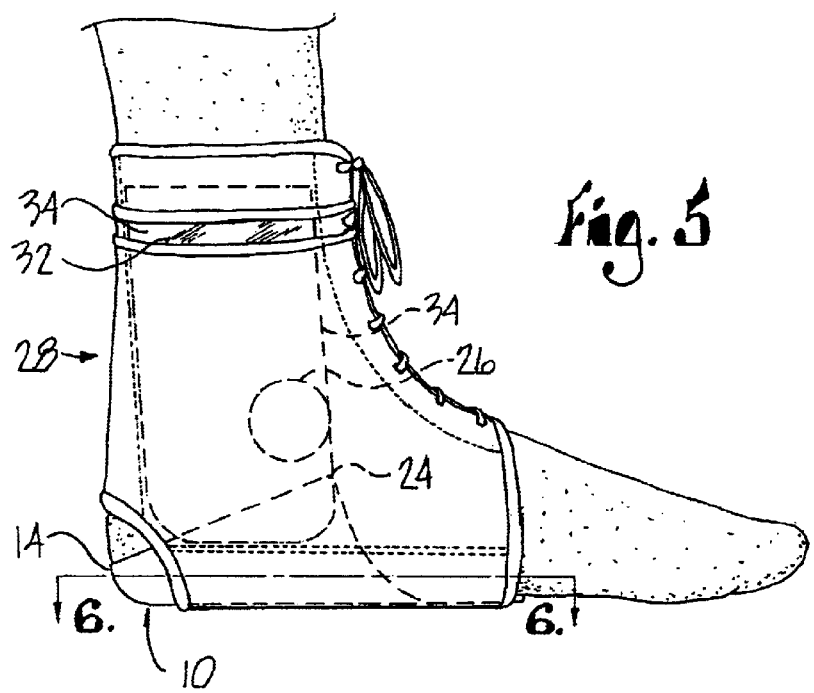
FIG. 5 is a side elevational view of the entire ankle support as applied to the foot of a wearer, the lateral side wall of the stabilizer being shown in broken lines within the flexible sheath.
Figure 6:
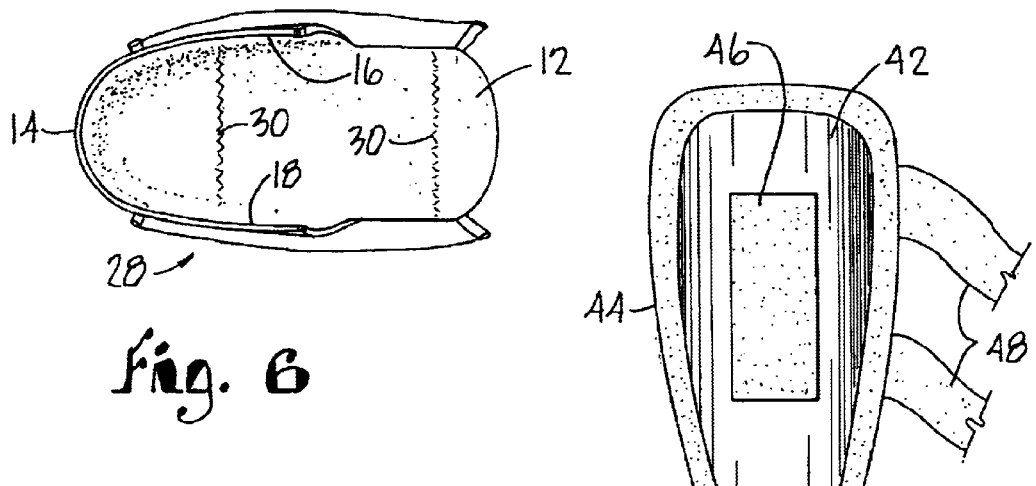
FIG. 6 is a horizontal, cross-sectional view taken along line 6—6 of FIG. 5 (the foot is not shown) revealing the base plate of the stabilizer and securement to the bottom of the sheath.

More particularly, FIGS. 5 and 6 show a preferred composite ankle support comprising a conventional lace-up ankle sheath 28 incorporating the semi-rigid stabilizer 10 which is secured within the sheath at the bottom thereof by two lines of zigzag stitching 30 through base plate 12 and the sheath material, which is typically a nylon and latex fabric. Each side of the sheath 28 (the lateral side being seen in FIG. 5) has a pocket 32 into which a flat, plate-like plastic stay 34 is inserted to provide medial and lateral rigidity. As may be seen by the broken line illustrations of the lateral stay 34 and lateral wall 18 in FIG. 5, the upper portions of the side walls 16 and 18 extend above the bottom of the stays 34 within the sheath 28 to a point just below the lateral and medial malleolus 26. By thus extending the side walls of the stabilizer 10 high on the medial and lateral sides, but not so high as to rub the ankle bones, the stabilizer effectively locks the heel bone to the fibula while providing relief at the rear as discussed above. Furthermore, as the stabilizer terminates at the anterior mouth 20, no restriction is imposed on movement of the foot throughout the arch and the ball of the foot. Accordingly, the stabilizer provides a heel lock without interfering with normal movement of the wearer's foot.

The semi-rigid stabilizer 10 may be molded from any suitable material such as, for example, subortholene or other plastics. The thickness of the base plate 12 and upstanding walls may be approximately 2 millimeters. This provides the wall structure with sufficient flexibility for comfort and fit, yet a memory that precludes permanent deformation.

Figure 7:
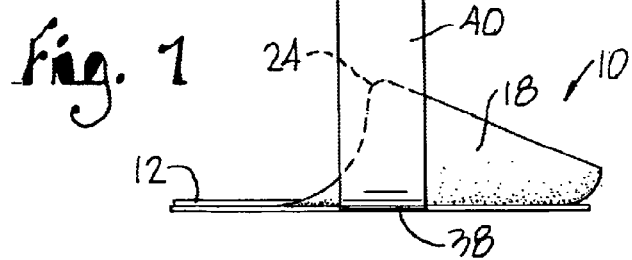
FIG. 7 is a side elevational view of an alternative embodiment of an ankle support incorporating the stabilizer of the present invention.

The stabilizer 10 of the present invention may also be employed with other conventional ankle supports that provide medial and lateral support but lack an effective heel lock. An alternative embodiment is shown in FIG. 7 where it may be seen that the stabilizer 10 is secured to the base or foot-plate 38 of a stirrup 40 depending from a pair of elongated support panels 42 which, when the support is applied to a wearer, provide rigidity on the medial and lateral sides of the ankle region. It may be appreciated that only the lateral panel 42 may be seen in the side elevational view of FIG. 7. Typically, each of the panels is faced with a layer of foam material 44 to provide comfortable supporting contact on each side of the ankle and leg. A Velcro strip 46 on the outer face of panel 42 secures straps 48 when they are wrapped around the support to hold it in place.

It is to be understood that while certain forms of this invention have been illustrated and described, it is not limited thereto except insofar as such limitations are included in the following claims and allowable equivalents thereof.

Having thus described the invention, what is claimed as new and desired to be secured by Letters Patent is as follows:

1. A stabilized ankle support comprising:
   a semi-rigid stabilizer having a base plate, a low rear wall and upstanding medial and lateral support walls for receiving a heel of a wearer,
   said walls presenting a generally U-shaped support structure conforming to the shape of a wearer's heel and having an anterior mouth from which a foot of a wearer projects when the ankle support is applied,
   each of said upstanding medial and lateral support walls having a peak portion at said anterior mouth adapted to extend into supporting relationship to a wearer beneath the medial and lateral malleolus and terminating below and proximate to the medial and lateral malleolus, and an upper edge that extends downwardly from said portion to said rear wall to provide relief at the rear wall of the stabilizer, and
   a flexible ankle support extending upwardly from said stabilizer for providing medial and lateral support while the stabilizer locks the heel to the fibula.

2. The ankle support as claimed in claim 1, wherein said stabilizer is of unitary construction whereby said walls and base plate are integral with one another.

3. The ankle support as claimed in claim 2, wherein said stabilizer is composed of a thin-walled, molded plastic material to provide sufficient flexibility for comfort and fit.

4. The ankle support as claimed in claim 1, wherein said upper edge of each of said medial and lateral walls defines an angle of approximately 25° to 30° with respect to said base plate.

5. The ankle support as claimed in claim 1, wherein said medial and lateral walls have front terminal edges extending downwardly from said peak portions thereof to said base plate to present said anterior mouth.

6. The stabilized ankle support as claimed in claim 1, wherein said low rear wall is approximately one-third the height of said peak portions.

7. The stabilized ankle support as claimed in claim 1, wherein said flexible ankle support comprises a lace-up ankle sheath adapted to secure said stabilizer to the foot of a wearer.

8. The stabilized ankle support as claimed in claim 1, wherein said flexible ankle support comprises a stirrup adapted to secure said stabilizer to the foot of a wearer.

9. A stabilized ankle support comprising:
   a semi-rigid, unitary stabilizer having a base plate, a low rear wall and upstanding medial and lateral support walls integral with one another for receiving a heel of a wearer,
   said walls presenting a generally U-shaped support structure conforming to the shape of a wearer's heel and having an anterior mouth from which a foot of a wearer projects when the ankle support is applied,
   each of said upstanding medial and lateral support walls having a peak portion at said anterior mouth adapted to extend into supporting relationship to a wearer beneath the medial and lateral malleolus and terminating below and proximate to the medial and lateral malleolus, an upper edge that extends downwardly from said portion to said rear wall to provide relief at the rear wall of the stabilizer, and a front terminal edge extending downwardly from said portion to said base plate to present said anterior mouth, and
   a flexible ankle support extending upwardly from said stabilizer for providing medial and lateral support while the stabilizer locks the heel to the fibula.

10. A stabilizer for use with an ankle support comprising:
    a flat, generally oval-shaped base plate having longitudinally opposing forward and rear ends and transversely opposed medial and lateral edges,
    a rear support wall projecting upwardly from said rear end of said base plate,
    a medial support wall projecting upwardly from said medial edge of said base plate,
    a lateral support wall projecting upwardly from said lateral edge of said base plate, said rear support wall having a height approximately one-third the height of said medial and lateral support walls, each of said medial and lateral support walls having a peak portion adapted to provide support to the ankle of a water beneath the medial and lateral malleolus and terminating below and proximate to the medial and lateral malleolus, each of said medial and lateral support walls extending angularly downwardly from said peak portion to said rear support wall, said medial, lateral and rear support walls presenting a generally U-shaped support structure adapted to receive a heel of a wearer, said support structure having a forward mouth from which a foot of a wearer projects when the stabilizer is applied to said heel, whereby said medial and lateral support walls, said base plate, and said rear support wall operate to lock said heel in position, thereby providing lateral and medial support to the ankle of a wearer, reducing interference with normal movement of a wearer's foot, and minimizing discomfort to said heel by providing a rear support wall of reduced height.

11. The stabilizer as claimed in claim 10, wherein said upper edge of each of said medial and lateral support walls defines an angle of approximately 25° to 30° with respect to said base plate.

12. The stabilizer as claimed in claim 10, further comprising a flexible ankle support attached to said stabilizer and adapted to secure said stabilizer to the foot of a wearer.

13. A stabilizer for use with an ankle support comprising:

a base plate having longitudinally opposing forward and rear ends and transversely opposed medial and lateral edges to provide undersupport to a heel of a wearer, a rear support wall projecting upwardly from said rear end of said base plate adapted to provide support along the rear of a wearer's heel, a medial support wall extending upwardly from said medial edge of said base plate and adapted to provide support along a medial side of an ankle of a wearer, said medial support wall presenting a free edge extending upwardly from said rear support wall to a peak below and proximate to the medial malleolus of a wearer's foot, a portion of said medial support wall below said peak adapted to support the ankle of a wearer beneath the malleolus on the medial side thereof, a lateral support wall extending upwardly from said lateral edge of said base plate and adapted to provide support along a lateral side of an ankle of a wearer, said lateral support wall presenting a free edge extending upwardly from said rear support wall to a peak below and proximate to the lateral malleolus of a wearer's foot, a portion of said lateral support wall below said peak adapted to support the ankle of a wearer beneath the malleolus on the lateral side thereof, said baseplate and medial, lateral and rear support walls cooperating to present a structure adapted to receive a heel of a wearer, whereby said medial and lateral support walls, said base plate, and said rear support wall operate to provide said respective support to the wearer.

14. The stabilizer as claimed in claim 13, wherein said rear support wall is of a height approximately one-third the height of said medial and lateral support walls.

15. The stabilizer as claimed in claim 13, wherein said free edge of each of said medial and lateral support walls defines an angle of approximately 25° to 30° with respect to said base plate.

* * * * *